(12) United States Patent
Robinson

(10) Patent No.: US 10,434,003 B2
(45) Date of Patent: Oct. 8, 2019

(54) LOWER EXTREMITY ISOLATING LEG BRACE

(71) Applicant: David Reid Robinson, Calgary (CA)

(72) Inventor: David Reid Robinson, Calgary (CA)

( * ) Notice: Subject to any disclaimer, the term of this patent is extended or adjusted under 35 U.S.C. 154(b) by 433 days.

(21) Appl. No.: 15/193,285

(22) Filed: Jun. 27, 2016

(65) Prior Publication Data

US 2017/0367866 A1   Dec. 28, 2017

(51) Int. Cl.
*A61F 5/01* (2006.01)
*A61F 5/30* (2006.01)

(52) U.S. Cl.
CPC .......... *A61F 5/0123* (2013.01); *A61F 5/0127* (2013.01); *A61F 5/0195* (2013.01); *A61F 5/30* (2013.01); *A61F 2005/0137* (2013.01); *A61F 2005/0167* (2013.01); *A61F 2005/0169* (2013.01)

(58) Field of Classification Search
CPC .............................. A61F 5/0123; A61F 5/0127
USPC ......................................... 602/16, 23, 26, 27
See application file for complete search history.

(56) References Cited

U.S. PATENT DOCUMENTS

| | | | |
|---|---|---|---|
| 1,660,721 A | 2/1928 | Schrag | |
| 2,111,018 A | 3/1938 | George | |
| 2,632,440 A * | 3/1953 | Hauser | A61F 5/0123 403/102 |
| 2,827,897 A | 3/1958 | Zygmunt | |
| 3,557,782 A | 1/1971 | Wafer | |
| 5,230,700 A | 7/1993 | Humbert et al. | |
| 5,300,016 A | 4/1994 | Marlatt | |
| 6,010,474 A * | 1/2000 | Wycoki | A61F 5/0102 602/23 |
| 6,024,713 A | 2/2000 | Barney | |
| 6,206,018 B1 | 3/2001 | Daniels, Jr. | |
| 6,997,891 B1 | 2/2006 | Vecsey | |
| 7,666,155 B1 | 2/2010 | Jensen | |
| 7,931,567 B2 | 4/2011 | Rosenberg et al. | |

(Continued)

FOREIGN PATENT DOCUMENTS

WO          03/013415          2/2003

OTHER PUBLICATIONS

International Search Report for Application No. PCT/IB2017/051694, dated Jun. 23, 2017.

(Continued)

*Primary Examiner* — Keri J Nelson
(74) *Attorney, Agent, or Firm* — Lewellyn Law, PLLC; Stephen Lewellyn

(57) ABSTRACT

A leg brace isolates a lower extremity of a leg to which the brace is secured. The leg brace includes an upper leg cuff and a lower leg cuff. Two upper struts are attached to opposite sides of the upper leg cuff and extend along the upper leg cuff. Two lower struts are attached to opposite sides of the lower leg cuff and extend along the lower leg cuff. One hinge pivotally connects one upper strut and one lower strut and a second hinge pivotally connects the other upper strut and the other lower strut. The hinges can be configured to have a limited and/or selectable degree of rotation (e.g., flexion and/or extension). Bottom ends of the lower struts extend beyond a user's foot of the leg to which the leg brace is attached. A foot is attached to each bottom end of the lower struts.

20 Claims, 5 Drawing Sheets

(56) References Cited

U.S. PATENT DOCUMENTS

| | | | |
|---|---|---|---|
| 8,172,781 B2 * | 5/2012 | Oddou | A61F 5/0125 |
| | | | 128/846 |
| 8,403,872 B2 | 3/2013 | Franke | |
| 8,540,655 B2 | 9/2013 | Franke et al. | |
| 8,672,865 B2 | 3/2014 | Franke | |
| 9,180,037 B1 | 11/2015 | Smith | |
| 9,204,985 B1 | 12/2015 | Fullerton | |
| 2008/0154165 A1 | 6/2008 | Ashihara | |
| 2010/0106065 A1 | 4/2010 | Ward | |
| 2011/0178446 A1 | 7/2011 | Benenati | |
| 2011/0319801 A1 | 12/2011 | Ital | |
| 2012/0330203 A1 * | 12/2012 | Jones | A61F 5/0123 |
| | | | 602/16 |
| 2014/0114218 A1 | 4/2014 | Baugh | |
| 2014/0114222 A1 * | 4/2014 | Volker | A61F 5/0123 |
| | | | 602/16 |

OTHER PUBLICATIONS

Canada Search Report for Application No. CA 2935571, dated Sep. 18, 2017.
Extended European Search Report of the European Patent Office, Application No. EP20170790660 20170323, dated Oct. 31, 2018, 7 pages.

* cited by examiner

LOWER EXTREMITY ISOLATING LEG BRACE

FIELD OF THE INVENTION

The present invention relates generally to orthotic devices, and more particularly, relating to a leg brace that isolates a lower leg from a user's weight.

BACKGROUND OF THE INVENTION

For various reasons, such as an injury, a person must keep weight off his or her knee, lower leg, and/or foot, and may use crutches or a wheelchair to move around. But crutches and wheelchairs can be cumbersome and may further impair the user's mobility. Accordingly, there is a need for a device that overcomes the drawbacks of crutches and wheelchairs while providing mobility to people with impairments of the lower extremities.

SUMMARY OF THE INVENTION

Embodiments of the present invention provide an orthotic device that is secured to a user's leg and is configured to isolate the lower extremities from bearing the user's weight.

In general, in one aspect, a leg brace is provided that is securable to a user's leg and that isolates the user's knee, lower leg, and foot from the user's weight by transferring the user's weight through load bearing struts and to the user's upper leg. In one embodiment, the leg brace includes an upper leg cuff, a pair of upper struts, a lower leg cuff, a pair of lower struts, a pair of hinges, and a pair of feet. The upper struts are attached to opposite sides of the upper leg cuff and extend along the length of the upper leg cuff. A bottom end of each upper strut extends beyond a bottom end of the upper leg cuff. Similarly, the lower struts are attached to opposite sides of the lower leg cuff and extend along the length of the lower leg cuff. A top end of each lower leg strut extends beyond a top end of the lower leg cuff and a bottom end of each lower leg strut extends beyond a bottom end of the lower leg cuff and beyond the foot of the user's leg to which the leg brace is secured. The hinges pivotally connect the bottom end and the top end of corresponding upper and lower struts. And the feet are attached to the bottom end of the lower struts.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

For a better understanding of the invention, its operating advantages and the specific objects attained by its uses, reference should be had to the accompanying drawings and descriptive matter in which there are illustrated embodiments of the invention.

BRIEF DESCRIPTION OF THE DRAWINGS

The following drawings illustrate by way of example and are included to provide further understanding of the invention for the purpose of illustrative discussion of the embodiments of the invention. No attempt is made to show structural details of the embodiments in more detail than is necessary for a fundamental understanding of the invention, the description taken with the drawings making apparent to those skilled in the art how the several forms of the invention may be embodied in practice. Identical reference numerals do not necessarily indicate an identical structure. Rather, the same reference numeral may be used to indicate a similar feature of a feature with similar functionality. In the drawings.

DETAILED DESCRIPTION OF THE INVENTION

Figure 1:
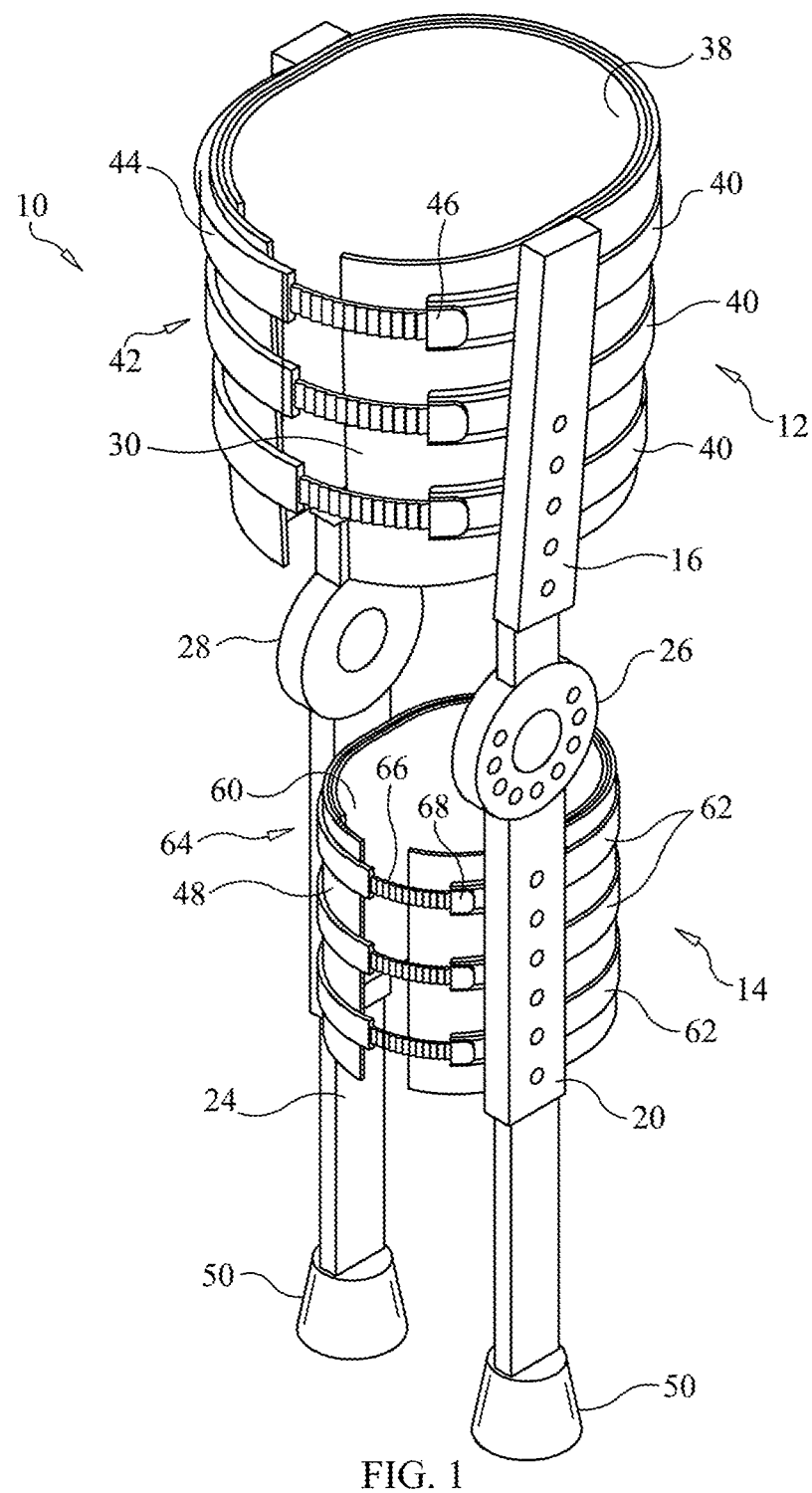
FIG. 1 is a perspective view of a leg brace that is constructed in accordance with the principles of an embodiment of the present invention.
Figure 2:
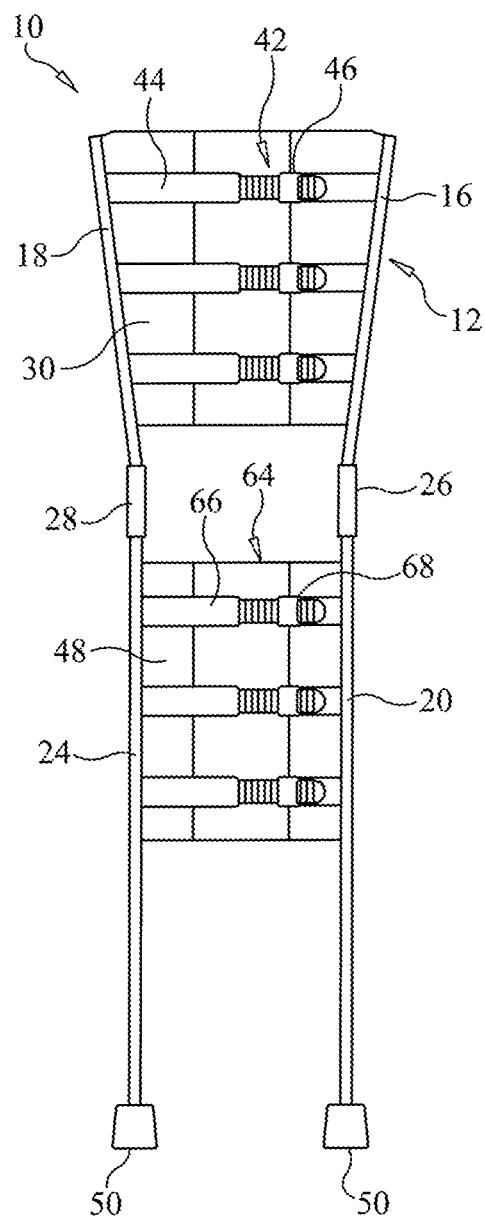
FIG. 2 is a front elevation view of the leg brace.
Figure 3:
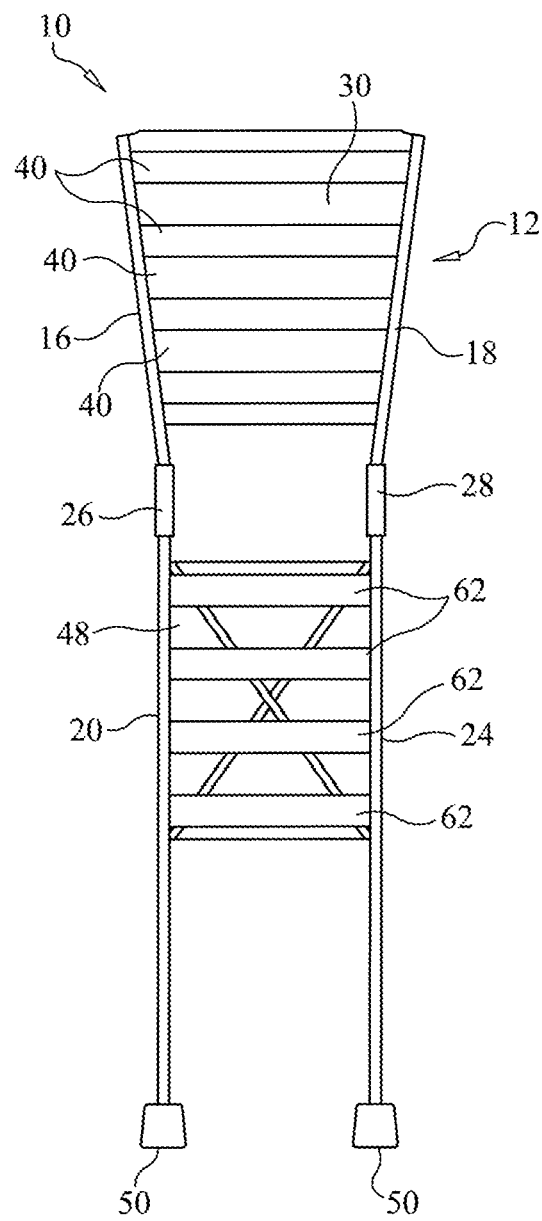
FIG. 3 is a rear elevation view of the leg brace.
Figure 4:
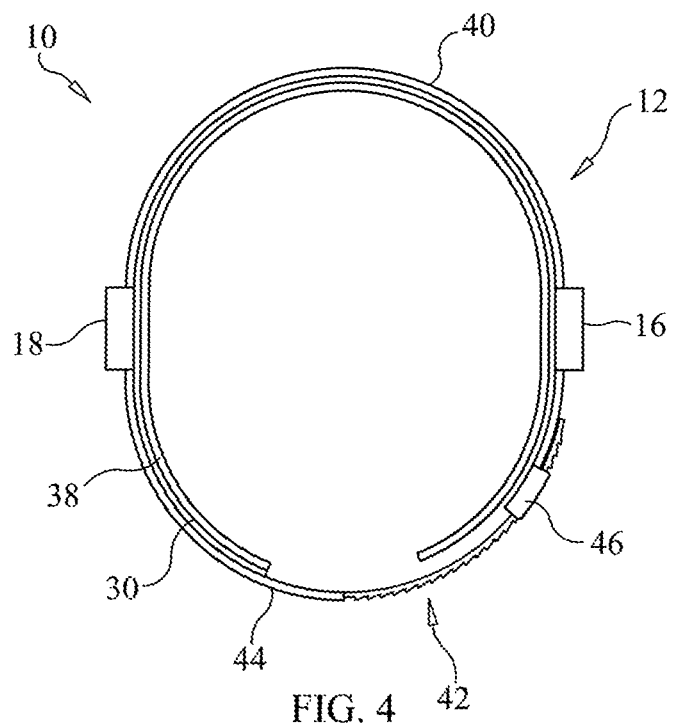
FIG. 4 is a top plan view of an upper leg cuff of the leg brace.
Figure 5:
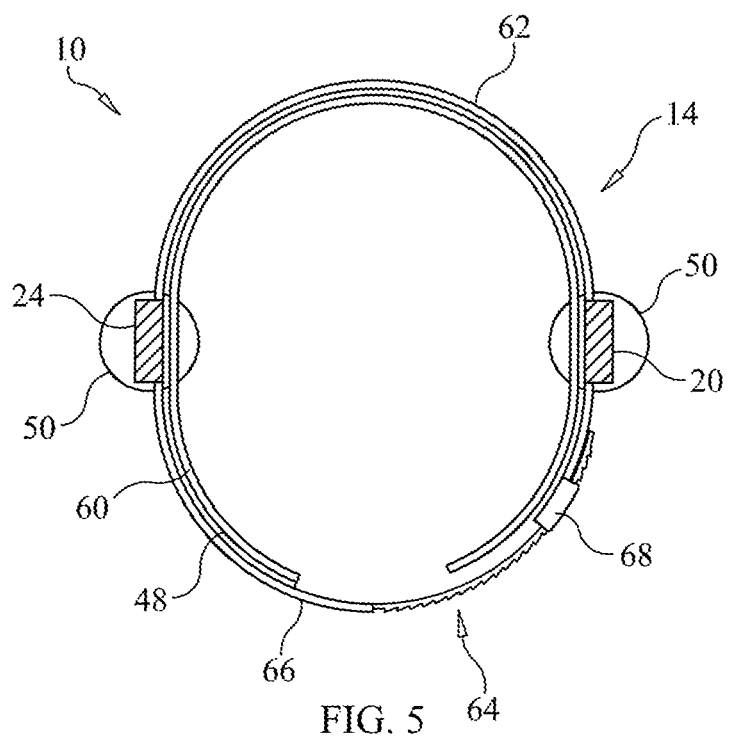
FIG. 5 is a top plan view of a lower leg cuff of the leg brace.

With reference to FIGS. 1-8, there is representatively illustrated a new leg brace 10 that is constructed in accordance with an embodiment of the present invention. Any directional references in this description, such as top or bottom, right or left, upper or lower, vertical, or horizontal are intended for convenience of the description, and by itself does not limit the present invention or any of its components to any particular position or spatial orientation.

Leg brace 10 includes an upper leg cuff 12, a lower leg cuff 14, upper struts 16 and 18, lower struts 20 and 24, and hinges 26 and 28. As will be described in further detail below, upper leg cuff 12 is designed to be securely attached to a user's thigh and bear the weight of a user by transferring the user's weight along the thigh. Whereas the lower leg cuff 14 is not load bearing. Rather, the lower leg cuff 14 provides lateral and forward support such that cuff moves with the user's lower leg so as to maintain correct positioning of the lower struts 20 and 24 relative to the user's foot.

Leg cuff 12 includes a shell 30 that is generally frustoconical shaped and is constructed of a pliable sheet material so as to conform to the taper and profile of a user's thigh while retaining its general frustoconical shape. The pliable sheet material may comprise, for example, polymers, plastics, carbon fiber, glass fiber, aramid fiber, para-aramid fiber, or other suitable materials that are capable of conforming to the shape of a user's thigh while retaining the frustoconical shape of shell 30. Shell 30 is open at its front end which allows the cuff to be slipped over and around a user's thigh, and may have a length so as to extend partially along or the entire length of the user's thigh.

Upper struts 16 and 18 are attached to the shell 30 at diametrically opposed locations on either side of the shell opening and extend vertically along and past a lower end of the shell where the struts are connected to hinges 26 and 28, respectively. Struts 16 and 18 have a lengthwise direction that is generally parallel to the length of a user's thigh when leg cuff 12 is attached to the user. Struts 16 and 18 are constructed of one or more rigid materials that are capable of supporting a user's weight. Such materials may include, for example, aluminum, aluminum alloy, titanium, titanium alloy, carbon fiber, wood, aramid fiber, para-aramid fiber, fiberglass, and combinations thereof. In addition, struts 16 and 18 may be constructed so that their lengths are adjustable to match the length of the person's thigh and position hinges 26 and 28 approximate the user's knee.

Figure 7:
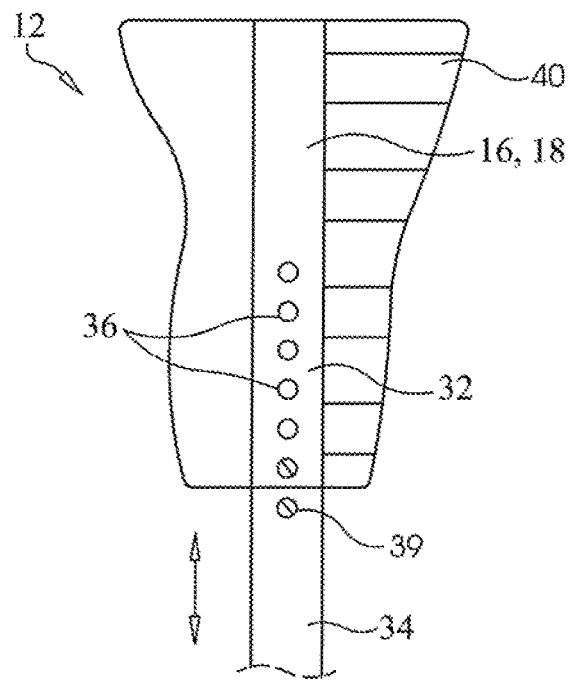
FIG. 7 is a partial view of an upper strut of the leg brace.

As best shown in FIG. 7, in the depicted embodiment, struts 16 and 18 each include a rectangular shaped first strut member 32 into which a rectangular shaped second strut member 34 is slidably received in a telescoping fashion relative to the first strut member. Member 32 includes a plurality of holes 36 that removably receive a pin, such as spring biased pin 39 located on member 34, for adjustably fixing the relative position of the members.

Leg cuff 12 further includes one or more pads, representatively shown as a single pad 38, disposed along the interior surface of shell 30. Pad 38 may comprise elastomeric and/or resilient materials including, for example, polyurethane, polyethylene, neoprene, ethylene, foam, silicone, rubber, and the like. Pad 38 may be removably attached to the interior surface of shell 30 by cooperating fasteners, such as, for example touch fasteners.

Leg cuff 12 further includes one or more support bands 40, representatively shown with four support bands that encircle a back portion of the shell 30 and extend between struts 16 and 18. Each support band 40 provides form support to the shell 30 to maintain the shell's frustoconical shape and is formed of a material such that the band is flexible and conforms to the profile of the user's thigh. In the preferred embodiment, each band is constructed of aluminum or aluminum alloy and has a thickness allowing the band to bend to conform to the shape of the user's thigh. However, it should be understood that other materials may be used to construct the support band 40 while retaining its desired function of providing support to the shell 30 and being flexible to conform to the profile of a user's thigh.

Leg cuff 12 further includes one or more strap or band fasteners 42, representatively shown with three band fasteners that are used to secure and tension the leg cuff on a user's thigh/upper leg. Band fastener may include a strap 44 and a buckle or cinch 46. The strap is 44 attached at one end thereof to the cuff 12 along one side of the shell opening and has a length such that the opposite free end is able to wrap around the cuff. The buckle or cinch 46 is attached to the cuff along the opposite side of the shell opening. The buckle or cinch 46 is configured to receive and releasably grip the strap 44. In use, strap 44 is threaded through or otherwise engaged with the buckle or cinch and pulled tight to secure the cuff to a user's thigh and apply a desired amount of tension. It should be understood that the invention should not limited to the depicted band fastener because other types of band fasteners could be used while meeting the same objective of securing and tensioning the cuff to a user's thigh. For example, the band fastener may have a strap that is affixed and tensioned across the cuff by touch fasteners or the like.

In the depicted embodiment, leg cuff 14 includes a shell 48 that is generally cylindrical shaped and is constructed of a pliable sheet material so as to have its diameter adjusted to generally correspond to the thickness of a lower leg. The pliable sheet material may comprise, for example, polymers, plastics, carbon fiber, glass fiber, aramid fiber, para-aramid fiber, or other suitable materials that are capable of bending. Shell 48 is open at its front end which allows the cuff to be slipped over and around a user's lower leg, and may have a length so as to extend partially along or the entire length of the user's lower leg.

Lower struts 20 and 24 are attached to the shell 48 at diametrically opposed locations on either side of the shell opening and extend vertically along and past an upper end of the shell where the struts are connected to hinges 26 and 28, respectively. Similarly, struts 20 and 24 extend past a lower end of the shell 48 and have a rubber foot 50 secured to each end. Struts 20 and 24 have a lengthwise direction that is generally parallel to the length of a user's lower leg when the cuff 14 is attached to the user. Struts 20 and 24 are constructed of one or more rigid materials that are capable of supporting a user's weight. Such materials may include, for example, aluminum, aluminum alloy, titanium, titanium alloy, carbon fiber, wood, aramid fiber, para-aramid fiber, fiberglass, and combinations thereof. In addition, struts 20 and 24 may be constructed so that their lengths are adjustable to be greater than the length of the user's lower leg and foot so as to position the feet 50 at a position located beyond the user's foot.

Figure 8:
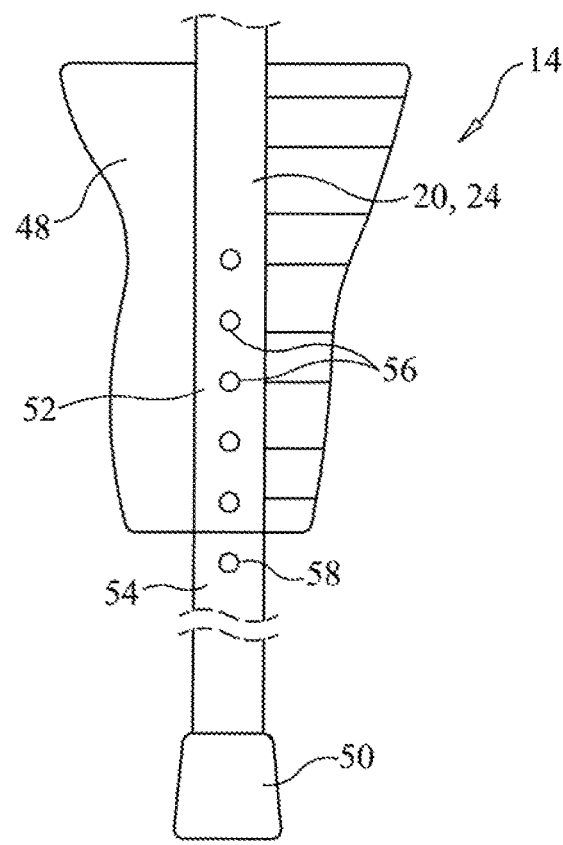
FIG. 8 is a partial view of a lower strut of the leg brace.

As best shown in FIG. 8, in the depicted embodiment, struts 20 and 24 each include a rectangular shaped first strut member 52 into which a rectangular shaped second strut member 54 is slidably received in a telescoping fashion relative to the first strut member. Member 52 includes a plurality of holes 56 that removably receive a pin, such as spring biased pin 58 located on member 54, for adjustably fixing the relative position of the members.

Leg cuff 14 further includes one or more pads, representatively shown as a single pad 60, disposed along the interior surface of shell 48. Pad 60 may comprise elastomeric and/or resilient materials including, for example, polyurethane, polyethylene, neoprene, ethylene, foam, silicone, rubber, and the like. Pad 60 may be removably attached to the interior surface of shell 48 by cooperating fasteners, such as, for example touch fasteners.

Leg cuff 14 further includes one or more support bands 62, representatively shown with four support bands that encircle a back portion of the shell 48 and extend between struts 20 and 24. Each support band 62 is rigid and provides form support to the shell 48 to maintain the shell's cylindrical shape. In the preferred embodiment, each band is constructed of aluminum or aluminum alloy of a thickness that prevents the band from readily bending. However, it should be understood that other materials may be used to construct the support band 62 while retaining its rigid, non-bending function.

Leg cuff 14 further includes one or more strap or band fasteners 64, representatively shown with three band fasteners that are used to secure and tension the thigh cuff on a user's thigh. Band fastener may include a strap 66 and a buckle or cinch 68. The strap is 66 attached at one end thereof to the cuff 14 along one side of the shell opening and has a length such that the opposite free end is able to wrap around the cuff. The buckle or cinch 68 is attached to the cuff along the opposite side of the shell opening. The buckle or cinch 68 is configured to receive and releasably grip the strap 66. In use, strap 66 is threaded through or otherwise engaged with the buckle or cinch and pulled to adjust the diameter of the cuff 14 and apply a desired amount of tension to a user's lower leg. It should be understood that the invention should not limited to the depicted band fastener because other types of band fasteners could be used while meeting the same objective of securing and tensioning the cuff to a user's calf. For example, the band fastener may have a strap that is affixed and tensioned across the cuff by touch fasteners or the like.

Hinges 26 and 28 may be of any orthotic hinge capable of pivotally connecting the ends of strut members or the like. Hinges 26 and 28 may be multi-axis hinge, such as, for example a ball-and-socket type hinge. In other embodiments, hinges 26 and 28 may be a single axis hinge. In addition, hinges 26 and 28 can be configured to have a limited and/or selectable degree of rotation (e.g., flexion and/or extension). Further, hinges 26 and 28 can be configured to have a resistive rotation to help people with reduced leg strength.

Figure 6:
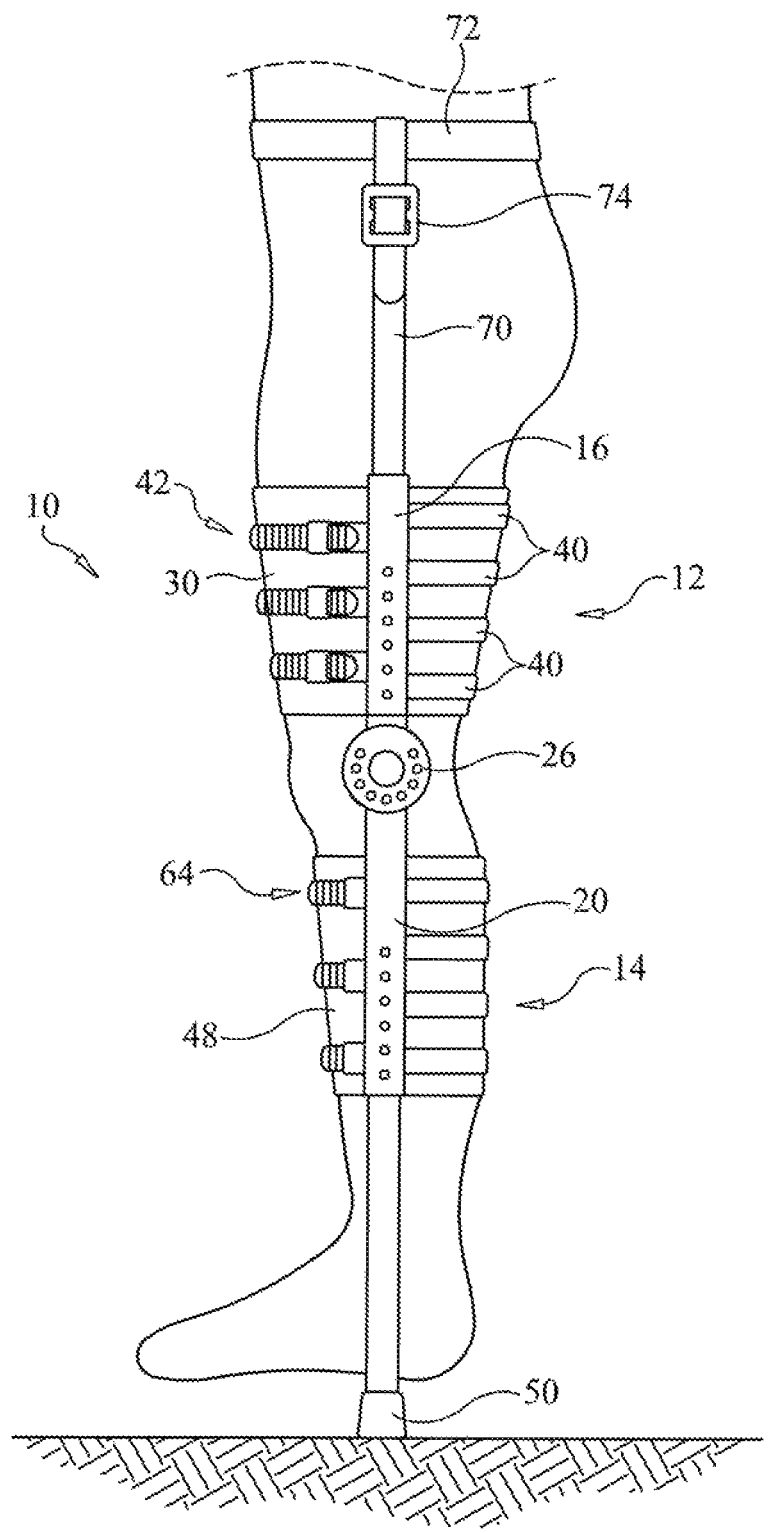
FIG. 6 is a side elevation view of a leg brace constructed in accordance with the principles of an embodiment of the present invention, shown in-use and secured to a user's leg.

With particular reference to FIG. 6, leg brace 10 may further include a support strap 70 that is attached at one end to strut 16 and is secured at its opposite end to a waist band 72. In one example, the end of the strap 70 can be looped around the waist band 72 and secured by buckle 74. In use, the strap 70 is tensioned so as to aid in maintaining positioning of the brace on a user's leg.

With continued reference to FIG. 6, when the leg brace 10 is attached and secured to a user's leg, hinges 26 and 28 are positioned about a user's knee and struts 20 and 24 have a length that locate feet 50 at a position beyond a user's foot. To this end, the user's weight is supported upon feet 50. The user's weight is transferred through struts 20 and 24 to struts 16 and 18 and then through leg cuff 12 and across a user's thigh, thereby isolating the lower leg and knee from any weight.

A number of embodiments of the present invention have been described. Nevertheless, it will be understood that various modifications may be made without departing from the spirit and scope of the invention. Accordingly, other embodiments are within the scope of the following claims.

What is claimed is:

1. A leg brace comprising:
  an upper leg cuff configured to bear the weight of a user by transferring the user's weight along the user's thigh, said upper leg cuff comprising a flexible upper shell;
  a first and second upper strut each having first and second ends, said first and second upper struts attached to opposite sides of said upper leg cuff and extending along the length of said upper leg cuff, said second ends of each of said first and second upper struts extending beyond a bottom end of said upper leg cuff;
  a lower leg cuff;
  a first and second lower strut each having first and second ends, said first and second lower struts attached to opposite sides of said lower leg cuff and extending along the length of said lower leg cuff, said first ends of said first and second lower struts extending beyond a top end of said lower leg cuff, and said second ends of said first and second lower struts extending beyond a bottom end of said lower leg cuff and beyond a foot of a user when said leg brace is attached to a user's leg, said lower cuff having a flexible front portion between said first and second lower struts and an unbendable back portion connected to and extending between said first and second lower struts, the unbendable back portion retaining its shape when said lower leg cuff is attached to the user's lower leg, thus preventing said lower leg cuff from being load-bearing while providing lateral and forward support such that said lower leg cuff moves with the user's lower leg;
  a first and second hinge, said first hinge pivotally connecting said second end of said first upper strut to said first end of said first lower strut, said second hinge pivotally connecting said second end of said second upper strut to said first end of said second lower strut; and
  a first and second foot, said first foot attached to said second end of said first lower strut, and said second foot attached to said second end of said second lower strut said first foot and said second foot configured to contact a walking surface to permit the user to avoid contacting the user's foot with the walking surface.

2. The leg brace of claim 1, wherein said first and second upper struts are adjustable in length.

3. The leg brace of claim 2, wherein said first and second upper struts each include a rectangular shaped first upper strut member into which a rectangular shaped second upper strut member is slidably received in telescoping fashion relative to said first upper strut member.

4. The leg brace of claim 1, wherein said first and second lower struts are adjustable in length.

5. The leg brace of claim 4, wherein said first and second lower struts each include a rectangular shaped first lower strut member into which a rectangular shaped second lower strut member is slidably received in telescoping fashion relative to said first lower strut member.

6. The leg brace of claim 1, wherein said upper leg cuff is frustoconical shaped.

7. The leg brace of claim 1, wherein said lower leg cuff is cylindrical shaped.

8. The leg brace of claim 1, further comprising:
  one or more tensioning bands on said upper leg cuff.

9. The leg brace of claim 8, wherein said one or more tensioning bands on said upper leg cuff comprise a band fastener.

10. The leg brace of claim 9, wherein said one or more tensioning bands of said upper leg cuff is three tensioning bands.

11. The leg brace of claim 9, wherein said band fastener includes a strap and a buckle or cinch attached to said upper leg cuff, said strap having a length such that its opposite free end is able to wrap around said upper leg cuff.

12. The leg brace of claim 1, further comprising:
  one or more tensioning bands on said lower leg cuff.

13. The leg brace of claim 12, wherein said one or more tensioning bands on said lower leg cuff comprise a band fastener.

14. The leg brace of claim 13, wherein said one or more tensioning bands of said lower leg cuff is three tensioning bands.

15. The leg brace of claim 13, wherein said band fastener includes a strap and a buckle or cinch attached to the lower leg cuff, said strap having a length such that its opposite free end is able to wrap around said lower leg cuff.

16. The leg brace of claim 1, wherein said upper leg cuff comprises:
  one or more upper support bands extending around a back portion of said upper shell, each of said one or more upper support bands being bendable to readily conform to a profile of a user's leg when said upper leg cuff is attached to a user's leg; and:
one or more pads attached to an interior surface of said upper shell.

17. The leg brace of claim 1, wherein said lower leg cuff comprises:
one or more pads attached to an interior surface of said lower shell.

18. The leg brace of claim 1, further comprising:
a support strap attached at one end to said first upper strut and securable at an opposite end to a waist belt.

19. The leg brace of claim 1, wherein said upper leg cuff is open at its front end.

20. The leg brace of claim 1, wherein said lower leg cuff is open at its front end.

\* \* \* \* \*